United States Patent
Matsuo

(10) Patent No.: US 11,778,113 B2
(45) Date of Patent: Oct. 3, 2023

(54) INFORMATION PROCESSING APPARATUS, IMAGE FORMING APPARATUS, AND NON-TRANSITORY COMPUTER READABLE MEDIUM

(71) Applicant: FUJIFILM Business Innovation Corp., Tokyo (JP)

(72) Inventor: Kota Matsuo, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 124 days.

(21) Appl. No.: 17/406,102

(22) Filed: Aug. 19, 2021

(65) Prior Publication Data
US 2022/0377193 A1    Nov. 24, 2022

(30) Foreign Application Priority Data
May 21, 2021  (JP) ................... 2021-086423

(51) Int. Cl.
*H04N 1/04*     (2006.01)
*H04N 1/00*     (2006.01)

(52) U.S. Cl.
CPC ..... *H04N 1/00724* (2013.01); *H04N 1/00779* (2013.01); *H04N 1/00732* (2013.01); *H04N 1/00734* (2013.01)

(58) Field of Classification Search
None
See application file for complete search history.

(56) References Cited

U.S. PATENT DOCUMENTS

| | | | |
|---|---|---|---|
| 2009/0245827 A1 | 10/2009 | Matsumoto | |
| 2019/0082067 A1* | 3/2019 | Tanigami | H04N 1/00689 |
| 2020/0016907 A1 | 1/2020 | Ogushi | |
| 2020/0192261 A1 | 6/2020 | Ogata et al. | |
| 2020/0264103 A1 | 8/2020 | Tomishima | |

FOREIGN PATENT DOCUMENTS

| | | |
|---|---|---|
| JP | 2019066830 | 4/2019 |
| JP | 2019166756 | 10/2019 |
| JP | 2020006628 | 1/2020 |
| JP | 2020097170 | 6/2020 |

OTHER PUBLICATIONS

"Search Report of Europe Counterpart Application", dated Nov. 24, 2021, p. 1-p. 9.

* cited by examiner

*Primary Examiner* — Cheukfan Lee
(74) *Attorney, Agent, or Firm* — JCIPRNET

(57) ABSTRACT

An information processing apparatus includes a processor configured to: obtain characteristic values including smoothness and basis weight of a recording medium; and identify the type of the recording medium on the basis of the smoothness and the basis weight.

14 Claims, 5 Drawing Sheets

FIG. 6

| TYPE | SETTING INFORMATION | | | |
|---|---|---|---|---|
| | TRANSFER VOLTAGE | TRANSFER PRESSURE | FIXING TEMPERATURE | ... |
| COATED PAPER | XX% | XX% | XX°C | ... |
| NON-EMBOSSED PAPER | YY% | YY% | YY°C | ... |
| EMBOSSED PAPER | ZZ% | ZZ% | ZZ°C | ... |
| ⋮ | ⋮ | ⋮ | ⋮ | ⋮ |

24A

INFORMATION PROCESSING APPARATUS, IMAGE FORMING APPARATUS, AND NON-TRANSITORY COMPUTER READABLE MEDIUM

CROSS-REFERENCE TO RELATED APPLICATIONS

This application is based on and claims priority under 35 USC 119 from Japanese Patent Application No. 2021-086423 filed May 21, 2021.

BACKGROUND

(i) Technical Field

The present disclosure relates to an information processing apparatus, an image forming apparatus, and a non-transitory computer readable medium.

(ii) Related Art

Japanese Unexamined Patent Application Publication No. 2020-006628 discloses a technique including a measurement unit, an image forming operation unit, a reading unit, and a medium identification unit. The measurement unit measures physical properties of a medium on which an image is formed. The image forming operation unit forms images on the medium. The reading unit reads the formed images. The medium identification unit identifies the type of the medium on the basis of the measurement results from the measurement unit and the reading results from the reading unit.

Japanese Unexamined Patent Application Publication No. 2020-097170 discloses a technique including a measurement unit, which measures a physical property of a medium, and a controller. The controller specifies combinations of basis weight and medium type on the basis of the measurement result from the measurement unit, and outputs the combinations as medium setting candidates for setting for image forming operation.

Techniques for image forming apparatuses have been proposed to set image formation control corresponding to each recording medium on which an image is formed by an image forming apparatus. In the techniques, multiple characteristic values of each recording medium, such as the smoothness and the basis weight of the recording medium, are measured. The characteristic values are used to identify the type of the recording medium, such as coated paper or uncoated paper.

Uncoated paper includes a recording medium such as high-quality paper, having a relatively small degree of surface unevenness, and a recording medium (for example, embossed paper obtained through embossing) having a relatively large degree of surface unevenness. Therefore, even when a recording medium is classified into uncoated paper, the recording medium has a different degree of surface unevenness. Thus, in transfer onto uncoated paper, an image forming apparatus needs to set different settings.

However, when the characteristics of a recording medium in the related art, which are the smoothness and the basis weight, are used, although it is possible to identify a recording medium as uncoated paper from the surface unevenness, it is difficult to determine the degree of surface unevenness of a recording medium.

SUMMARY

Aspects of non-limiting embodiments of the present disclosure relate to an information processing apparatus, an image forming apparatus, and a non-transitory computer readable medium which determine the degree of surface unevenness of a recording medium classified into uncoated paper.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided an information processing apparatus including a processor configured to: obtain characteristic values including smoothness and basis weight of a recording medium; and identify the type of the recording medium on the basis of the smoothness and the basis weight.

BRIEF DESCRIPTION OF THE DRAWINGS

Exemplary embodiment of the present disclosure will be described in detail based on the following figures, wherein:

FIG. 6 is a diagram illustrating an exemplary setting-information database according to the present exemplary embodiment.

DETAILED DESCRIPTION

Figure 1:
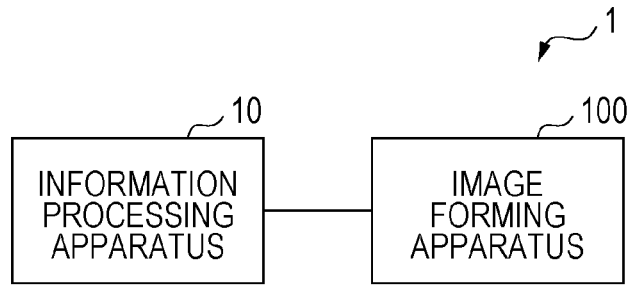
FIG. 1 is a block diagram illustrating an exemplary schematic configuration of an information processing system according to the present exemplary embodiment.

Exemplary embodiment for carrying out the present disclosure will be described in detail below by referring to the drawings.

FIG. 1 is a diagram illustrating the schematic configuration of an information processing system 1 according to the present exemplary embodiment. As illustrated in FIG. 1, the information processing system 1 includes an information processing apparatus 10 and an image forming apparatus 100. The information processing apparatus 10 and the image forming apparatus 100 are communicatively connected to each other over a network. As the network, for example, the Internet, a local area network (LAN), or a wide area network (WAN) is used.

The information processing apparatus 10 is, for example, a terminal such as a personal computer or a server. The information processing apparatus 10 identifies the type of a recording medium from characteristic values (for example, the basis weight and the smoothness) of the recording medium, and transmits, to the image forming apparatus 100, information (hereinafter referred to as "setting information") about settings for forming an image in accordance with the type of the recording medium. The types of recording media according to the present exemplary embodiment include coated paper and uncoated paper which includes non-embossed paper and embossed paper. In accordance with the type of a recording medium, for example, the transfer voltage and the transfer pressure of the image forming apparatus are differently set. In accordance with the identified type of a recording medium, the information processing apparatus 10 according to the present exemplary embodiment transmits, as setting information, settings of the transfer voltage and the transfer pressure, which correspond to the type of the recording medium, to the image forming apparatus 100.

The image forming apparatus 100 is, for example, an apparatus such as a multifunction device which forms images on recording media. The image forming apparatus 100 obtains setting information from the information processing apparatus 10, and forms images by using the setting information.

Figure 2:
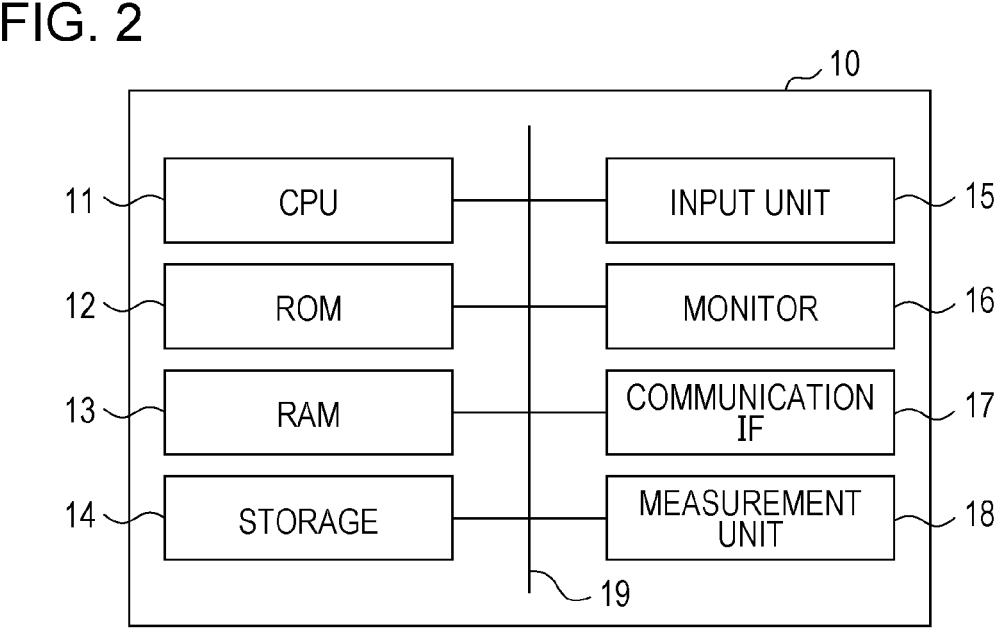
FIG. 2 is a block diagram illustrating an exemplary hardware configuration of an information processing apparatus according to the present exemplary embodiment.

Referring to FIG. 2, the configuration of the information processing apparatus 10 will be described. FIG. 2 is a block diagram illustrating an exemplary hardware configuration of the information processing apparatus 10 according to the present exemplary embodiment.

As illustrated in FIG. 2, the information processing apparatus 10 according to the present exemplary embodiment includes a central processing unit (CPU) 11, a read only memory (ROM) 12, a random access memory (RAM) 13, a storage 14, an input unit 15, a monitor 16, a communication interface (communication IF) 17, and a measurement unit 18. The CPU 11, the ROM 12, the RAM 13, the storage 14, the input unit 15, the monitor 16, the communication IF 17, and the measurement unit 18 are connected to each other through a bus 19. The CPU 11 is an exemplary processor.

The CPU 11 controls the entire information processing apparatus 10. In the ROM 12, for example, various programs, including an information processing program used in the present exemplary embodiment, and data are stored. The RAM 13 is a memory used as a work area in execution of the various programs. The CPU 11 loads, for execution, programs, which are stored in the ROM 12, onto the RAM 13, and thus identifies the types of recording media. Examples of the storage 14 include a hard disk drive (HDD), a solid state drive (SSD), and a flash memory. The storage 14 may store the information processing program and the like. The input unit 15 is, for example, a mouse and a keyboard for receiving input of characters and the like. The monitor 16 displays the identified type of a recording medium and setting information. The communication IF 17 receives/transmits data.

The measurement unit 18 includes an optical sensor for measuring the smoothness and an ultrasonic wave sensor for measuring the basis weight. For example, the measurement unit 18 measures a ratio of specular reflected light to diffuse reflected light on the surface of a recording medium, and thus measures the smoothness. The measurement unit 18 measures a ratio of transmitted ultrasonic waves to radiated ultrasonic waves, and thus measures the basis weight. The smoothness indicates the degree of roughness of the surface of a recording medium. The basis weight indicates grams (density) per square meter of a recording medium.

In the present exemplary embodiment, the smoothness and the basis weight are obtained as characteristic values of a recording medium. However, this is not limiting. For example, an electrical resistance value, air permeability, a coefficient of friction, and stiffness may be obtained as characteristic values.

Figure 3:
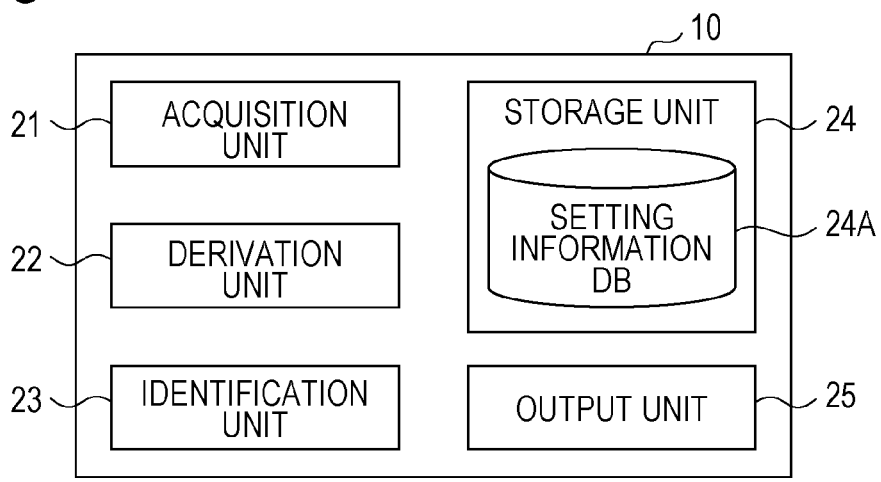
FIG. 3 is a block diagram illustrating an exemplary functional configuration of an information processing apparatus according to the present exemplary embodiment.

Referring to FIG. 3, the functional configuration of the information processing apparatus 10 will be described. FIG. 3 is a block diagram illustrating an exemplary functional configuration of the information processing apparatus 10 according to the present exemplary embodiment.

As illustrated in FIG. 3, the information processing apparatus 10 includes an acquisition unit 21, a derivation unit 22, an identification unit 23, a storage unit 24, and an output unit 25. The CPU 11 executes the information processing program, thus functioning as the acquisition unit 21, the derivation unit 22, the identification unit 23, the storage unit 24, and the output unit 25.

The acquisition unit 21 acquires the smoothness and the basis weight as characteristic values of a recording medium.

By using the obtained smoothness and basis weight, the derivation unit 22 derives a value obtained by weighting the smoothness by the basis weight (hereinafter referred to as "weighted smoothness"). The weighted smoothness according to the present exemplary embodiment indicates a value derived on the basis of the smoothness and the basis weight. The weighted smoothness will be described as being a value obtained by dividing the smoothness by the basis weight. However, this is not limiting. The smoothness may be multiplied by the basis weight, or the basis weight may be divided by the smoothness. Alternatively, the smoothness may be multiplied or divided by a coefficient predetermined in accordance with the basis weight.

The identification unit 23 uses the smoothness, the basis weight, and the weighted smoothness to identify the type of a recording medium by discriminating coated paper from uncoated paper, and further, for uncoated paper, discriminating non-embossed paper from embossed paper. Coated paper is paper such as glossy paper having a coating applied on the surface of a recording medium. Non-embossed paper is paper, such as high-quality paper and Kent paper, without a coating applied on the surface of a recording medium. Embossed paper is paper having a large degree of surface unevenness, for example, due to embossing. Embossed paper, having no coating applied on the surface, is classified into uncoated paper. However, compared with high-quality paper and Kent paper which are classified into uncoated paper which is the same type as embossed paper, embossed paper has a larger degree of surface unevenness. Therefore, in the present exemplary embodiment, high-quality paper and Kent paper, which are classified into uncoated paper, are discriminated from embossed paper on the basis of the degree of surface unevenness.

The identification unit 23 determines whether a recording medium is coated paper by using the smoothness. For example, if the smoothness is greater than a predetermined threshold, the identification unit 23 determines the type of the recording medium to be coated paper. If the smoothness is equal to or less than the predetermined threshold, the identification unit 23 discriminates non-embossed paper from embossed paper by using the weighted smoothness.

Figure 4:
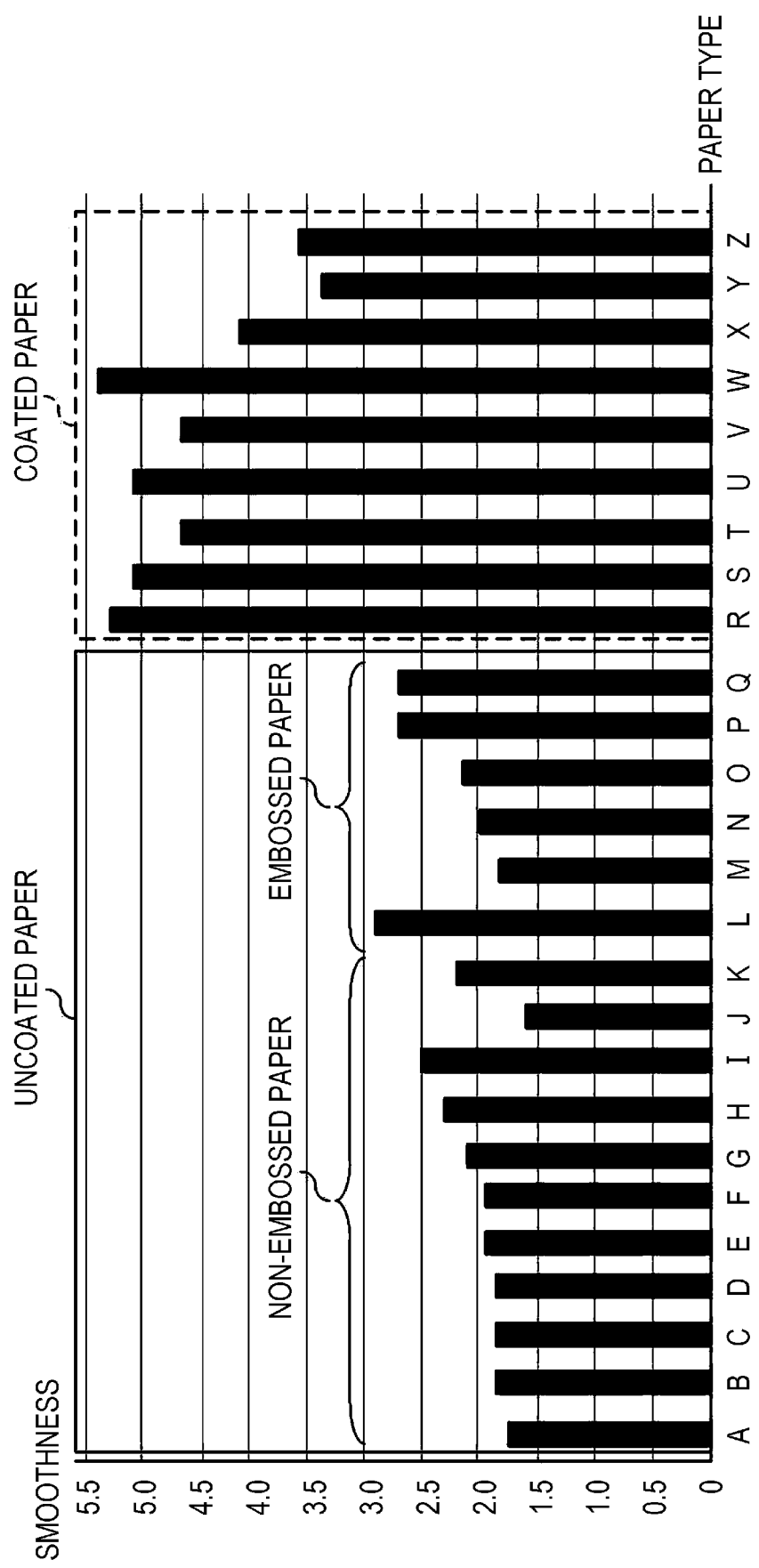
FIG. 4 is a graph illustrating examples of smoothness of the respective types of recording media according to the present exemplary embodiment.
Figure 5:
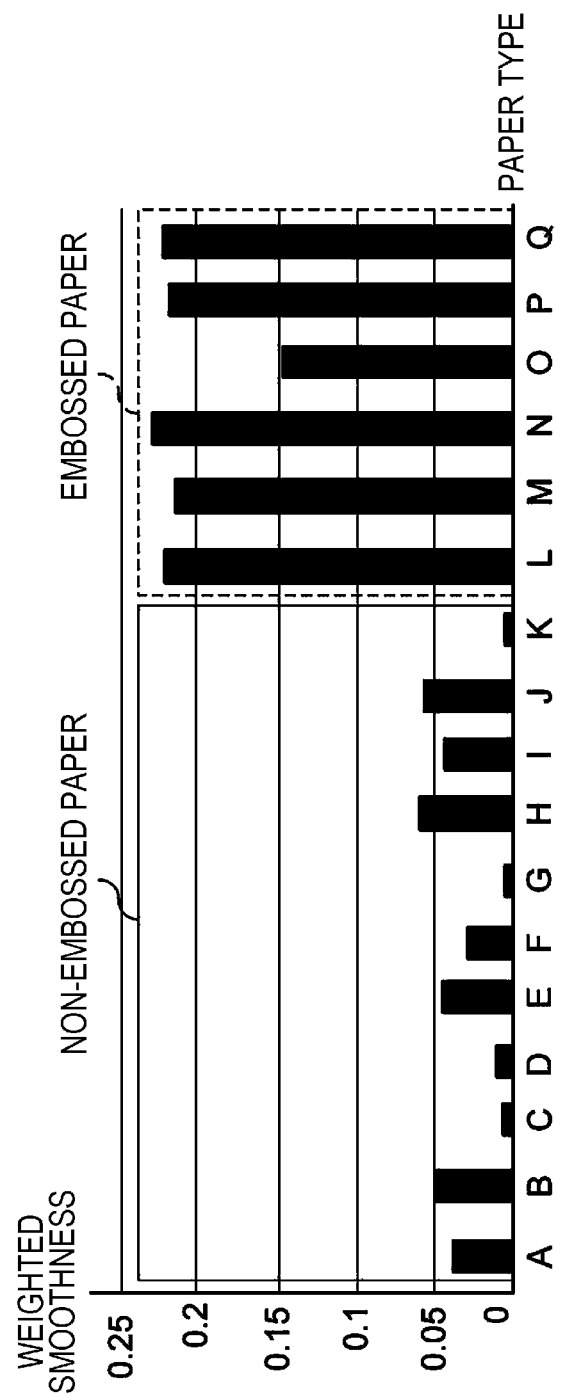
FIG. 5 is a graph illustrating examples of weighted smoothness of the respective types of recording media according to the present exemplary embodiment.

By referring to FIGS. 4 and 5, the smoothness of non-embossed paper and embossed paper which are classified into the same type, uncoated paper, will be described. FIG. 4 is an exemplary graph of smoothness of each recording medium. FIG. 5 is an exemplary graph of weighted smoothness of each recording medium. A larger degree of smoothness indicates a smaller degree of roughness of the surface of a recording medium. A larger degree of weighted smoothness indicates a larger degree of roughness of the surface of a recording medium.

As illustrated in FIG. 4, for example, when the smoothness of coated paper is compared with that of uncoated paper, and when, for uncoated paper, the smoothness of non-embossed paper is compared with that of embossed paper, there occurs a large difference between the smoothness of coated paper and that of uncoated paper. For example, as described above, there is a method of radiating light and measuring smoothness from the reflected light. That is, in the case of a surface having a large degree of smoothness (a dense surface), the reflected light, which is obtained through reflection on the surface of a recording medium, has a large amount of specular reflected light and a small amount of diffuse reflected light. In the case of a surface having a small degree of smoothness (a sparse surface), the reflected light, which is obtained through reflection on the surface of a recording medium, has a small amount of specular reflected light and a large amount of diffuse reflected light. Through detection of this difference in the reflected light, coated paper may be discriminated from uncoated paper. In contrast, for uncoated paper, the smoothness of non-embossed paper is not different from that of embossed paper by a large amount.

In contrast, for example, as illustrated in FIG. 5, in comparison using the weighted smoothness which is obtained by weighting the smoothness by the basis weight, non-embossed paper tends to have a small degree of weighted smoothness, whereas embossed paper tends to have a larger degree of weighted smoothness than non-embossed paper. Therefore, as illustrated in FIG. 5, the weighted smoothness, which is obtained by weighting the smoothness by the basis weight, may be used to identify embossed paper.

If the weighted smoothness is greater than a predetermined threshold, the identification unit 23 determines that the type of the recording medium is embossed paper. If the weighted smoothness is equal to or less than the predetermined threshold, the identification unit 23 determines that the type of the recording medium is non-embossed paper.

In the present exemplary embodiment, if the weighted smoothness is greater than the predetermined threshold, the recording medium is determined to be embossed paper. However, this is not limiting. For example, when the weighted smoothness, which is derived by dividing the basis weight by the smoothness, is less than a predetermined threshold, the recording medium may be determined to be embossed paper.

The storage unit 24 stores setting information for each recording medium. For example, as illustrated in FIG. 6, the storage unit 24 stores a setting-information database (hereinafter referred to as a "setting information DB") 24A. The setting information DB 24A stores the type and the setting information. The type indicates the type of a recording medium. The setting information indicates information about settings for attributes, such as the transfer voltage, the transfer pressure, and the fixing temperature.

The setting information DB 24A according to the present exemplary embodiment stores setting information for each type of recording medium. However, this is not limiting. In accordance with characteristic values of the smoothness and the basis weight, further segmented setting information may be stored. For example, setting information may be stored for each type of recording medium and each characteristic value of recording medium, such as setting information in which, as the basis weight becomes larger, a smaller transfer pressure is set.

The output unit 25 obtains, from the storage unit 24, setting information in accordance with the type of a recording medium which is identified by the identification unit 23, and outputs the setting information to the image forming apparatus 100.

Figure 7:
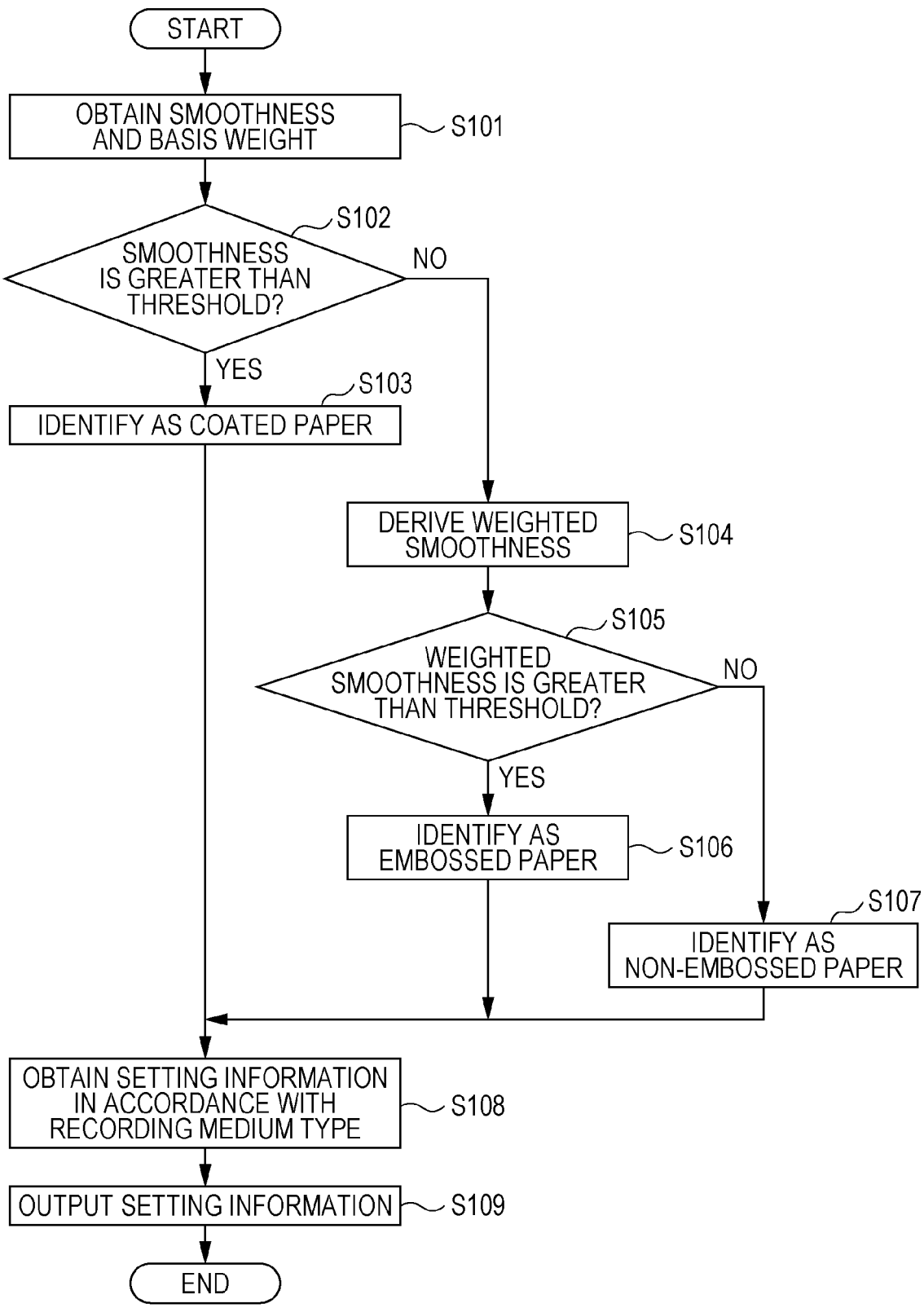
FIG. 7 is a flowchart of a process of identifying the type of a recording medium according to the present exemplary embodiment.

Referring to FIG. 7, operation of the information processing apparatus 10 according to the present exemplary embodiment will be described. FIG. 7 is a flowchart of an exemplary process of identifying the type of a recording medium according to the present exemplary embodiment. The CPU 11 reads, for execution, the information processing program from the ROM 12 or the storage 14, and the information processing program described in FIG. 7 is executed. The information processing program described in FIG. 7 is executed, for example, when an instruction to identify a recording medium is input from the image forming apparatus 100.

In step S101, the CPU 11 obtains the smoothness and the basis weight as characteristic values of the recording medium.

In step S102, the CPU 11 determines whether the smoothness is greater than the predetermined threshold. If the smoothness is greater than the predetermined threshold (YES in step S102), the CPU 11 causes the process to proceed to step S103. In contrast, if the smoothness is not greater than the predetermined threshold (the smoothness is equal to or less than the predetermined threshold; NO in step S102), the CPU 11 causes the process to proceed to step S104.

In step S103, the CPU 11 identifies the type of the recording medium as coated paper.

In step S104, the CPU 11 derives the weighted smoothness by using the smoothness and the basis weight.

In step S105, the CPU 11 determines whether the weighted smoothness is greater than the predetermined threshold. If the weighted smoothness is greater than the predetermined threshold (YES in step S105), the CPU 11 causes the process to proceed to step S106. In contrast, if the weighted smoothness is not greater than the predetermined threshold (the weighted smoothness is equal to or less than the predetermined threshold; NO in step S105), the CPU 11 causes the process to proceed to step S107.

In step S106, the CPU 11 identifies the type of the recording medium as embossed paper.

In step S107, the CPU 11 identifies the type of the recording medium as non-embossed paper.

In step S108, the CPU 11 obtains setting information in accordance with the identified type of the recording medium.

In step S109, the CPU 11 outputs the obtained setting information to the image forming apparatus 100.

As described above, the present exemplary embodiment enables determination, for uncoated paper, as to whether a recording medium has a large degree or a small degree of surface unevenness.

The information processing apparatus 10 according to the present exemplary embodiment is separate from the image forming apparatus 100. However, this is not limiting. The information processing apparatus 10 may be included in the image forming apparatus 100.

The image forming apparatus 100 according to the present exemplary embodiment obtains setting information from the information processing apparatus 10. However, this is not limiting. The identified type of a recording medium may be obtained.

The image forming apparatus 100 according to the present exemplary embodiment forms an image by using the obtained setting information. However, this is not limiting. The obtained setting information may be stored.

In the present exemplary embodiment, setting information corresponding to the identified recording medium is output. However, this is not limiting. The setting information corresponding to the identified recording medium may be displayed. Alternatively, it may be determined whether the setting information corresponding to the identified recording medium corresponds to settings that are input by a user. For example, when settings, which are input by a user, do not correspond to the identified recording medium (for example, the recording medium which is set on the image forming apparatus 100), a message indicating that the settings do not correspond to the recording medium is transmitted to prompt change of the settings.

The present disclosure is described by using the embodiments. The present disclosure is not limited to the scope described in the embodiments. Various changes and improvements may be added to the embodiments without departing from the gist of the present disclosure. Embodiments obtained by adding the changes and improvements are also encompassed in the technical scope of the present disclosure.

In the embodiments above, the term "processor" refers to hardware in a broad sense. Examples of the processor include general processors (e.g., CPU: Central Processing Unit) and dedicated processors (e.g., GPU: Graphics Processing Unit, ASIC: Application Specific Integrated Circuit, FPGA: Field Programmable Gate Array, and programmable logic device).

In the embodiments above, the term "processor" is broad enough to encompass one processor or plural processors in collaboration which are located physically apart from each other but may work cooperatively. The order of operations of the processor is not limited to one described in the embodiments above, and may be changed.

In the present exemplary embodiment, the information processing program is installed in a storage. However, this is not limiting. The information processing program according to the present exemplary embodiment may be provided by recording the information processing program in a computer-readable recording medium. For example, the information processing program according to the present exemplary embodiment of the present disclosure may be provided by recording the information processing program in an optical disc, such as a compact disc (CD)-ROM or a digital versatile disc (DVD)-ROM. The information processing program according to the present exemplary embodiment of the present disclosure may be provided by recording the information processing program in a semiconductor memory, such as a Universal Serial Bus (USB) memory or a memory card. The information processing program according to the present exemplary embodiment may be obtained from an external apparatus through a communication line connected to the communication IF.

What is claimed is:

1. An information processing apparatus comprising:
 a processor configured to:
  obtain characteristic values including smoothness and basis weight of a recording medium; and
  identify a type of the recording medium on a basis of the smoothness and the basis weight, wherein a weighted smoothness based on the smoothness and the basis weight is used to identify embossed paper as the type of the recording medium.

2. The information processing apparatus according to claim 1,
 wherein the processor is configured to:
  identify the type of the recording medium as the embossed paper when the weighted smoothness is greater than a predetermined threshold.

3. The information processing apparatus according to claim 2,
 wherein the processor is configured to:
  use at least one of the smoothness, the basis weight, or the weighted smoothness to identify the type of the recording medium as coated paper, uncoated paper, or the embossed paper.

4. The information processing apparatus according to claim 3,
 wherein the processor is configured to:
  further output a setting of an image forming apparatus, the setting corresponding to the type of the recording medium.

5. The information processing apparatus according to claim 4,
 wherein the processer is configured to:
  output, as the setting, a setting of either or both of transfer voltage and transfer pressure in accordance with the type of the recording medium.

6. The information processing apparatus according to claim 2,
 wherein the processor is configured to:
  further output a setting of an image forming apparatus, the setting corresponding to the type of the recording medium.

7. The information processing apparatus according to claim 6,
 wherein the processer is configured to:
  output, as the setting, a setting of either or both of transfer voltage and transfer pressure in accordance with the type of the recording medium.

8. The information processing apparatus according to claim 1,
 wherein the processor is configured to:
  use at least one of the smoothness, the basis weight, or the weighted smoothness to identify the type of the recording medium as coated paper, uncoated paper, or the embossed paper.

9. The information processing apparatus according to claim 8,
 wherein the processor is configured to:
  further output a setting of an image forming apparatus, the setting corresponding to the type of the recording medium.

10. The information processing apparatus according to claim 9,
 wherein the processer is configured to:
  output, as the setting, a setting of either or both of transfer voltage and transfer pressure in accordance with the type of the recording medium.

11. The information processing apparatus according to claim 1,
 wherein the processor is configured to:
  further output a setting of an image forming apparatus, the setting corresponding to the type of the recording medium.

12. The information processing apparatus according to claim 11,
 wherein the processer is configured to:
  output, as the setting, a setting of either or both of transfer voltage and transfer pressure in accordance with the type of the recording medium.

13. An image forming apparatus comprising:
 a processer configured to:

obtain characteristic values including smoothness and basis weight of a recording medium; and identify a type of the recording medium on a basis of the smoothness and the basis weight, wherein a weighted smoothness based on the smoothness and the basis weight is used to identify embossed paper as the type of the recording medium.

14. A non-transitory computer readable medium storing a program causing a computer to execute a process for information processing, the process comprising:

obtaining characteristic values including smoothness and basis weight of a recording medium; and identifying a type of the recording medium on a basis of the smoothness and the basis weight, wherein a weighted smoothness based on the smoothness and the basis weight is used to identify embossed paper as the type of the recording medium.

* * * * *